United States Patent
Kaibel et al.

(10) Patent No.: US 6,846,389 B2
(45) Date of Patent: Jan. 25, 2005

(54) METHOD FOR DISTILLATIVE SEPARATION OF MIXTURES CONTAINING TETRAHYDROFURAN, γ-BUTYROLACTONE AND/OR 1,4-BUTANEDIOL

(75) Inventors: Gerd Kaibel, Lampertheim (DE); Alexander Weck, Freinsheim (DE); Ralf-Thomas Rahn, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/258,938
(22) PCT Filed: May 3, 2001
(86) PCT No.: PCT/EP01/04974
§ 371 (c)(1), (2), (4) Date: Oct. 29, 2002
(87) PCT Pub. No.: WO01/85708
PCT Pub. Date: Nov. 15, 2001

(65) Prior Publication Data
US 2003/0106786 A1 Jun. 12, 2003

(30) Foreign Application Priority Data
May 4, 2000 (DE) .......................... 100 21 703

(51) Int. Cl.[7] .............................. B01D 3/14; B01D 3/42; C07D 307/08; C07D 307/33
(52) U.S. Cl. ................. 203/1; 203/75; 203/77; 203/78; 203/80; 203/99; 203/DIG. 9; 203/DIG. 19; 549/295; 568/868; 568/888
(58) Field of Search .............. 203/2, 99, DIG. 19, 203/DIG. 9, 1, 75, 77, 78, 80, 100; 202/158; 196/111; 549/295, 429, 509; 568/868, 888, 864

(56) References Cited
U.S. PATENT DOCUMENTS

| | | |
|---|---|---|
| 4,912,236 A | 3/1990 | Palm et al. |
| 4,919,765 A | 4/1990 | Wilkes et al. |
| 4,940,805 A | 7/1990 | Fischer et al. |
| 5,030,328 A | 7/1991 | Fischer et al. |
| 5,310,954 A | 5/1994 | Hiles et al. |
| 5,342,488 A * | 8/1994 | Gosch et al. .................. 203/80 |
| 6,075,153 A | 6/2000 | Bergfeld et al. |

FOREIGN PATENT DOCUMENTS

| | | |
|---|---|---|
| EP | 255 400 | 2/1988 |
| EP | 301 852 | 2/1989 |
| WO | 91/01981 | 2/1991 |
| WO | 97/43234 | 11/1997 |
| WO | 97/43242 | 11/1997 |

OTHER PUBLICATIONS

Triantafyilou et al., "The Design and Optimisation of Fully Thermally Coupled Distillation Columns"Trans I Chem, vol. 70, Manrch 1992, pp. 118–132.□□.*

Mutalib et al., "Operation and Control of Dividing Wall Distillation Columns" Trans I Cheme, vol. 76, Part A, Mar. 1998, pp. 319–334.*

Mutalib, et al "Operation and Control of Dividing Wall Distillation Columns" Trans I Chem E, vol. 76, Part A, Mar. 1998, PP. 308–318.*

Ullmann's Ency.Ind.Chem., 6th Ed., 1999, Electronic Release, Chapter Maleic and Fumaric Acids, Maleic Anhydride.

* cited by examiner

Primary Examiner—Virginia Manoharan
(74) Attorney, Agent, or Firm—Keil & Weinkauf

(57) ABSTRACT

In a process for the continuous fractional distillation of mixtures comprising tetrahydrofuran, γ-butyrolactone and/or 1,4-butanediol to give at least three fractions, the fractionation is carried out in an assembly of distillation columns comprising at least one dividing wall column or at least one assembly of thermally coupled conventional distillation columns.

17 Claims, 8 Drawing Sheets

US 6,846,389 B2

METHOD FOR DISTILLATIVE SEPARATION OF MIXTURES CONTAINING TETRAHYDROFURAN, γ-BUTYROLACTONE AND/OR 1,4-BUTANEDIOL

The present invention relates to a continuous process for the fractional distillation of mixtures comprising tetrahydrofuran, γ-butyrolactone and/or 1,4-butanediol to give at least three fractions.

In the industrial preparation of 1,4-butanediol, tetrahydrofuran and γ-butyrolactone, increasing use is made of hydrocarbons having at least four carbon atoms as economical raw materials. Important starting materials are benzene, n-butenes and n-butane. In a first stage, the hydrocarbons are oxidized in the gas phase over heterogeneous catalysts to give maleic anhydride. An overview of current processes is given in Ullmann's Encyclopedia of Industrial Chemistry, 6th Edition, 1999 Electronic Release, Chapter "Maleic and Fumaric Acids, Maleic Anhydride". The maleic anhydride formed is condensed from the gas stream by cooling or absorbed in water or organic absorbents. Depending on the work-up chosen, maleic anhydride, maleic acid, its diesters, its monoesters or mixtures thereof are obtained. These compounds are subsequently hydrogenated, either as such or after appropriate conversion into maleic anhydride, maleic acid, its diesters, its monoesters or mixtures thereof, in the liquid or gas phase over heterogeneous catalysts. Such heterogeneously catalyzed hydrogenations are described, for example, in EP-A 0 304 696 for maleic anhydride, succinic anhydride or their acids, diesters or monoesters in the liquid phase, in WO 97/24346 for maleic anhydride, succinic anhydride or their acids in the gas phase, in WO 97/43242 for dialkyl maleates in the gas phase and in WO 97/43234 for maleic anhydride in the gas phase. Depending on the catalyst used and the reaction conditions set, hydrogenation products comprising tetrahydrofuran, γ-butyrolactone and/or 1,4-butanediol are obtained.

While 1,4-butanediol is an important intermediate in the production of polyurethanes, polybutylene terephthalates and tetrahydrofuran, tetrahydrofuran is used mainly for preparing polytetrahydrofuran. In addition, it serves as a versatile solvent, for example for resins and polyvinyl chloride. γ-Butyrolactone is an important starting material for numerous syntheses, for example the preparation of N-ethylpyrrolidone, pyrrolidone, polyvinylpyrrolidone and herbicides, and is used as a versatile solvent for polymers.

For their further uses, tetrahydrofuran, γ-butyrolactone and 1,4-butanediol have to be obtained in very pure form. This is particularly true of tetrahydrofuran if it is to be polymerized to polytetrahydrofuran and subsequently spun into fibers. Work-up by distillation has become established as a standard operation for the purification steps. According to the prior art, it is achieved by means of a plurality of distillation columns which are connected in a conventional manner for the fractionation of multicomponent mixtures.

The continuous fractional distillation of multicomponent mixtures is carried out using various process variants. In the simplest case, the feed mixture is separated into a low-boiling top fraction and a high-boiling bottom fraction. In the fractionation of feed mixtures to give more than 2 fractions, this process variant requires the use of a plurality of distillation columns. In order to limit the outlay in terms of apparatus, columns having side offtakes for liquid or vapor are used where possible in the fractionation of multicomponent mixtures. However, a disadvantage is that the products taken off at the side offtakes are never completely pure. The use of conventional side offtake columns is therefore restricted to cases in which contaminated side products are permissible or can be redistilled by means of additional, downstream columns.

Thus, according to CHEM SYSTEMS, volume 91S15, "Butanediol/Tetrahydrofuran", April 1993, pages 54–59, a total of six distillation columns are used for the work-up of mixtures obtained in the hydrogenation of diethyl maleate. In the first column, a tetrahydrofuran/water mixture is taken off at the top and is separated in a second column into tetrahydrofuran and water. The bottom product from the first column is passed to the third column and there ethanol is taken of at the top. In the fourth column, further by-products are taken off at the top, γ-butyrolactone and diethyl succinate are separated from one another in the fifth column and, finally, 1,4-butanediol and high boilers are separated from one another in the sixth column.

For the separation of tetrahydrofuran from a mixture comprising water, tetrahydrofuran and alcohols, it has been found to be useful to employ a "two-pressure distillation" which is described in WO 91/01981. Here, a phase comprising water, tetrahydrofuran and alcohols is taken off at the top of the first column and is passed to the second column. The second column is operated at a higher pressure than the first and pure tetrahydrofuran is separated off at the bottom. The phase taken off at the top is recirculated to the first column.

It is an object of the present invention to find a process for the continuous fractional distillation of mixtures comprising tetrahydrofuran, γ-butyrolactone and/or 1,4-butanediol, where at least one fraction comprises tetrahydrofuran, γ-butyrolactone and/or 1,4-butanediol and the process makes it possible to isolate the desired products in high purity with at the same time a low energy consumption and low capital costs of the plant. A further object of the present invention is to find a flexible and at the same time simple method of carrying out the process which ensures reliable operation of the process so that the high purity requirements are met and the energy consumption is low even in the case of fluctuations in the amount of the product streams and their composition.

We have found that these objects are achieved by a process for the continuous fractional distillation of mixtures comprising tetrahydrofuran, γ-butyrolactone and/or 1,4-butanediol to give at least three fractions, in which the fractionation is carried out in an assembly of distillation columns comprising at least one dividing wall column or at least one assembly of thermally coupled conventional distillation columns.

For the purposes of the present invention, an assembly of distillation columns means at least one dividing wall column or at least two conventional distillation columns. If the assembly comprises more than one column, the columns are connected to one another via the further passage and/or the mutual exchange of mass flows (product streams) and/or energy flows. Distillation columns are apparatuses having at least one feed point and at least two offtake points in which the rectification region is located between vaporizer and condenser, where part of the liquid condensate formed in the condenser moves downward as runback through the rectification region in countercurrent to the vapor rising from the vaporizer, and which thus make it possible to separate mixtures by distillation.

An essential aspect of the process of the present invention is that the assembly of distillation columns comprises at least one dividing wall column and/or at least one assembly of thermally coupled conventional distillation columns. Dividing wall columns are special distillation columns having at least one feed point and at least three offtake points in which the rectification region is located between vaporizer and condenser, where part of the liquid condensate formed in the condenser moves downward as runback through the rectification region in countercurrent to the vapor rising from the vaporizer, and which have at least one longitudinal dividing facility (dividing wall) in a subregion of the column below and/or above the feed point to prevent transverse mixing of liquid stream and/or vapor stream and which thus make it possible to separate mixtures by distillation. The basic principle of dividing wall columns is well-known and is described in U.S. Pat. No. 2,471,134, in EP-A0 122 367 or in C. Kaibel, Chem. Eng. Technol. Vol. 10, 1987, pages 92 to 98.

BRIEF DESCRIPTION OF THE DRAWINGS

FIG. 1 schematically shows the general basic structure of a dividing wall column. It has at least one lateral feed point on one side of the dividing wall and at least three offtake points at the other side of the dividing wall. The streams are denoted as follows:
(A, B, C) feed mixture which is fed in at the feed point
(A) low-boiling fraction which is taken off at the top offtake,
(B) intermediate-boiling fraction which is taken off at the side offtake,
(C) high-boiling fraction which is taken off at the bottom offtake.

Figure 1:
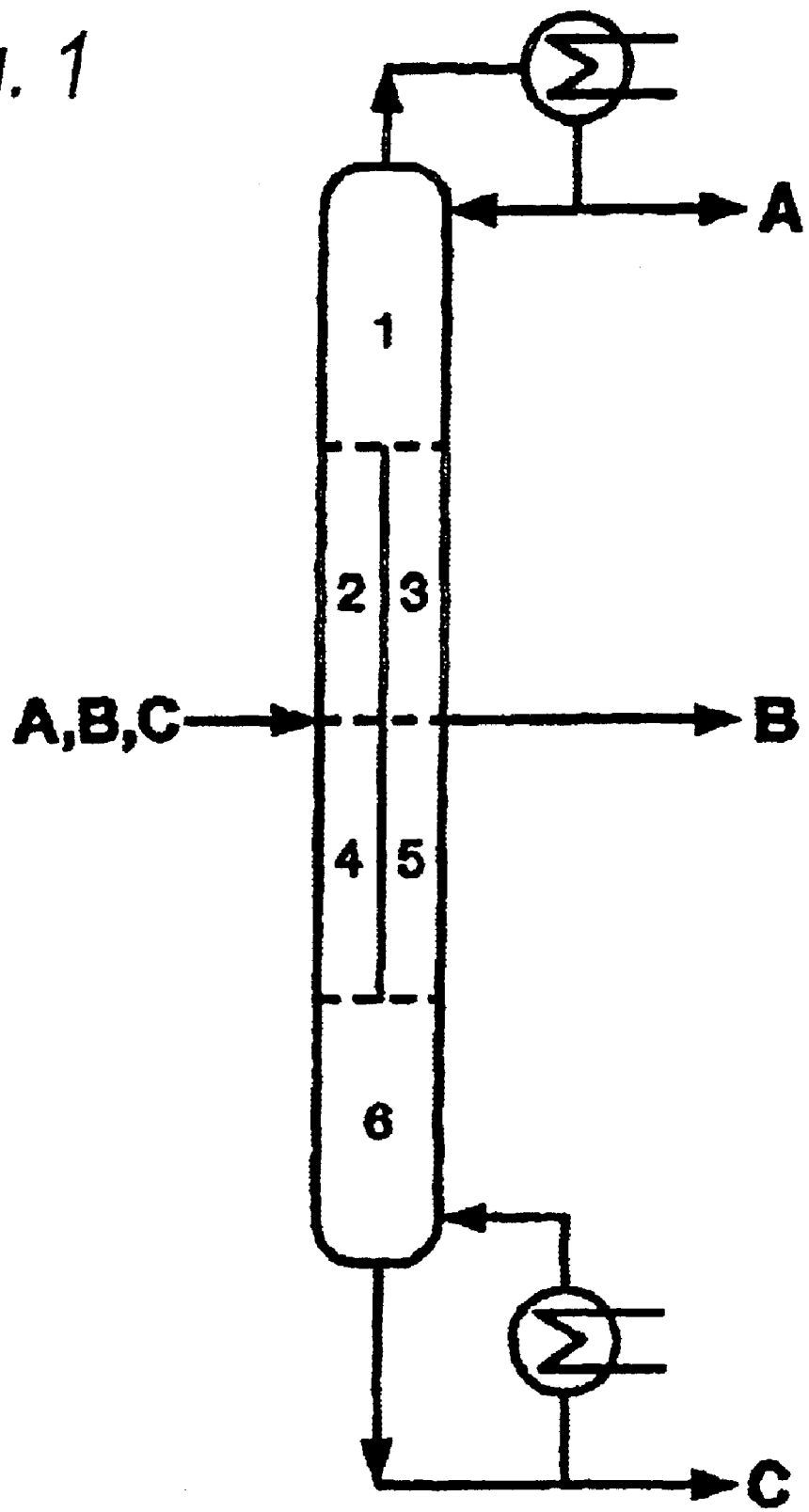
FIG. 1: schematically shows the general basic structure of a dividing wall column.

The region within the dividing wall column can be roughly divided into the following six subregions:
(1) top section
(2) upper feed section
(3) upper offtake section
(4) lower feed section
(5) lower offtake section
(6) bottom section.

Since, in this type of construction, transverse mixing of liquid stream and/or vapor stream is prevented in the region of the dividing wall, it is possible to obtain even side products in pure form. This generally reduces the total number of distillation columns required in the fractionation of multicomponent mixtures. In addition, capital costs and also energy can be saved when using dividing wall columns instead of a simple series arrangement of two conventional distillation columns (cf. M. Knott, Process Engineering, Vol. 2, 1993, February, pages 33 and 34). The term conventional distillation columns is used to refer to all distillation columns which do not contain a dividing wall.

In the process of the present invention, dividing wall columns can also be replaced by or combined with an assembly of thermally coupled conventional distillation columns. In thermally coupled conventional distillation columns, mass and energy flows are mutually exchanged, so that a significant saving of energy compared to a simple series arrangement of conventional distillation columns is possible. As an alternative to a dividing wall column, preference is given to an arrangement of two thermally coupled distillation columns. An overview of various assemblies is given, for example, in G. Kaibel et al., Chem.-Ing.-Tech., Vol. 61, 1989, pages 16 to 25, and G. Kaibel et al., Gas Separation & Purification, Vol. 4, 1990, June, pages 109 to 114.

Figure 2:
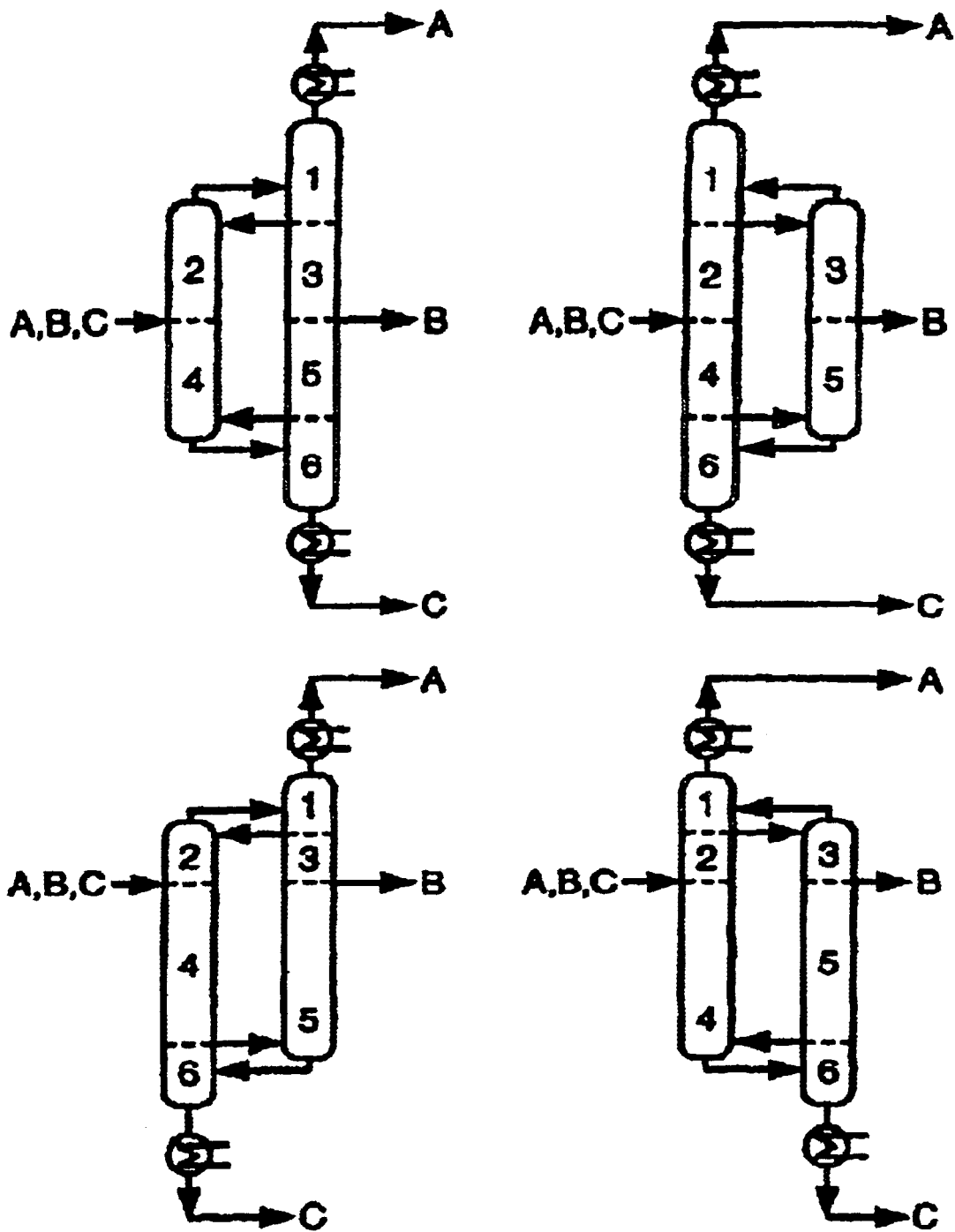
FIG. 2 and FIG. 3: show without implying a limitation, schematic examples of possible assemblies of in each case two conventional distillation columns which correspond to a dividing wall column.
Figure 3:
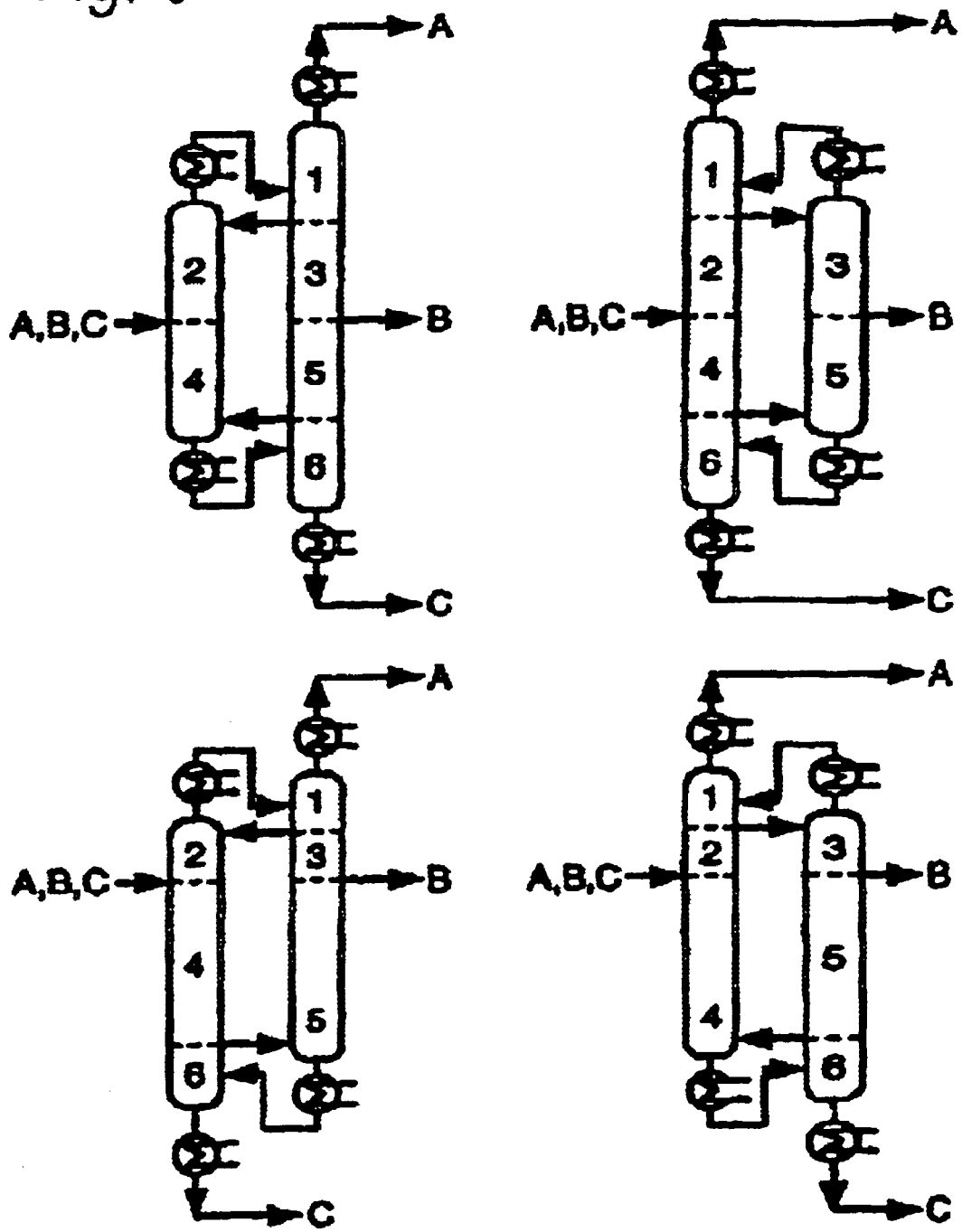

FIGS. 2 and 3 show, without implying a limitation, schematic examples of possible assemblies of in each case two conventional distillation columns which correspond to a dividing wall column. The designations (A, B, C), (A), (B), (C) and (1) to (6) are as defined above. In the process of the present invention, dividing wall columns can in principle be replaced by the assemblies shown schematically in FIG. 2 or 3.

If existing conventional distillation columns are used, the most suitable form of connection is generally chosen according to the number of theoretical plates of the columns available. Continuing use is advantageously made of existing apparatuses, for example vaporizers or condensers, as shown in the assemblies in FIGS. 2 and 3. It is possible to choose configurations which allow only liquid connecting flows between the individual distillation columns. These specific arrangements offer the advantage of the two distillation columns being able to be operated under different pressures so that they can be matched better to the temperature level of existing heating and cooling facilities. In general, the column from which the low-boiling fraction is taken will be operated at a pressure higher than that of the column from which the high-boiling fraction is taken.

The use of two thermally coupled conventional distillation columns is advantageous, for example, when the individual columns are already present (e.g. in the conversion, refitting, expansion or modernization of an existing plant) or when the two columns are to be operated at different pressures.

In the case of thermally coupled conventional distillation columns, it can be advantageous for the bottoms from the first distillation column to be partly or completely vaporized in an additional vaporizer before passing them to the second distillation column. This prevaporization is particularly useful when the bottoms from the first distillation column comprise relatively large amounts of intermediate boilers. In this case, the prevaporization can be carried out at a lower temperature level and the load on the vaporizer of the second distillation column can be reduced. Furthermore, this measure significantly reduces the load on the stripping section of the second distillation column. The prevaporized stream can be fed to the second distillation column as a two-phase stream or in the form of two separate streams.

Furthermore, both in the case of dividing wall columns and in the case of thermally coupled conventional distillation columns, it can be advantageous to subject the feed stream to prevaporization and subsequently to introduce it into the distillation column as a two-phase stream or in the form of two streams. This prevaporization is particularly useful when the feed stream comprises relatively large amounts of low boilers. The prevaporization can significantly reduce the load on the stripping section of the distillation column.

In the process of the present invention, it is possible to use conventional distillation columns or conventional assemblies of main columns with side columns acting as rectification or stripping column in addition to the arrangement of distillation columns according to the present invention. Although these additional columns likewise make it possible to obtain the desired products in high purity, they generally have a higher energy consumption.

Since dividing wall columns have a simpler construction than thermally coupled conventional distillation columns, they generally have the advantage of lower capital costs. For this reason, the use of dividing wall columns is preferred over the use of thermally coupled conventional distillation columns in the process of the present invention, particularly when new plants are being constructed.

The feed mixture used in the process of the present invention comprises at least one of the components tetrahydrofuran, γ-butyrolactone and 1,4-butanediol. The composition of the mixture can vary widely and depends on the way in which it is produced. In general, the concentration of tetrahydrofuran is from 0 to 70% by weight, that of γ-butyrolactone is from 0 to 85% by weight and that of 1,4-butanediol is from 0 to 85% by weight. The mixture generally further comprises additional components. The process by means of which the mixture has been obtained is not critical for the success of the process of the present invention.

The mixture is preferably obtained from the hydrogenation of maleic anhydride, maleic acid, its diesters or its monoesters. The preferred mixture can further comprise the water which has been formed in the reaction or which may have been added and also by-products and coproducts, for example alcohols (e.g. methanol, ethanol, 1-propanol, 2-propanol, 1-butanol, 2-butanol, 2-methyl-2-propanol, 2-methyl-1-propanol from the esters used), succinic acid, succinic anhydride, succinic esters, butyric acid, butyric esters, butadiene, methacrolein, dihydrofurans (e.g. 2,3-dihydrofuran) or glycol ethers (e.g. dibutylene glycol). The water content is typically from 0 to 35% by weight.

The tetrahydrofuran-, γ-butyrolactone- and/or 1,4-butanediol-containing mixture to be used in the process of the present invention is particularly preferably obtained by heterogeneously catalyzed gas-phase hydrogenation of the abovementioned components, as is known, for example, from WO 97/24346, WO 97/43242 and WO 97/43234. The product stream obtained in the hydrogenation is conveyed from the hydrogenation reactor and is generally cooled. In the preferred gas-phase process, the desired products, water and the major part of the by-products are condensed out in this way. Unreacted hydrogen, inert gases (e.g. nitrogen and noble gases) and very low-boiling by-products remain in the gas phase and are separated off. The liquid mixture obtained in this way is then passed to the continuous fractional distillation of the present invention.

In the process of the present invention, the desired products tetrahydrofuran, γ-butyrolactone and/or 1,4-butanediol are separated off and isolated in high purity. For the purposes of the present invention, a high purity means a concentration of >99.8% by weight in the case of tetrahydrofuran, >99.5% by weight in the case of γ-butyrolactone and >99.3% by weight in the case of 1,4-butanediol. Depending on the desired embodiment of the process, all three products, any combination of two of the products or only one of the abovementioned products can be separated off and obtained in the desired purity.

In the process of the present invention, the fractional distillation results in at least three fractions. For the purposes of the present invention, a fraction is a product whose composition has been changed from that of the feed mixture by means of fractional distillation, with lower- and/or higher-boiling components having been separated off. In the specific example of a dividing wall column shown in FIG. 1, the product streams (A), (B) and (C) are designated as fractions. If two or three of the abovementioned products of value are isolated in the process of the present invention, the mixture is fractionated into more than three fractions.

For the purposes of further discussion, it is advantageous to divide the process of the present invention into distillation blocks. For the purposes of the present invention, a distillation block is an assembly comprising at least one distillation column, with the presence of further apparatuses such as pumps, heat exchangers or vessels also being possible. The process of the present invention comprises at least one distillation block selected from the group consisting of (B1) a distillation block for separating off tetrahydrofuran
(B2) a distillation block for separating off butyrolactone and
(B3) a distillation block for separating off 1,4-butanediol, where the desired products are preferably isolated in the order (B1) before (B2) before (B3), corresponding to their boiling points. Since the boiling points of the components to be separated off increase in this order, the operating pressures of the distillation columns can generally be chosen so that they decrease from (B1) through (B2) to (B3). Depending on the composition of the mixture to be fractionated and the desired requirements, the fractional distillation can comprise one distillation block (B1 or B2 or B3), two distillation blocks (B1–B2 or B1–B3 or B2–B3) or three distillation blocks (B1–B2–B3). It is also possible to deviate from this order. The various distillation blocks must be connected to one another via the mass flow of the mixture to be fractionated. It is also possible for mass flows to be passed back or passed on to previous or subsequent distillation blocks. Furthermore, coupling of the various distillation blocks in terms of energy is also possible and may be advantageous.

(B1) Distillation Block for Separating Off Tetrahydrofuran

The distillation block for separating off tetrahydrofuran in the process of the present invention preferably comprises at least two distillation columns, with the pressure in the distillation column in which the pure tetrahydrofuran product is separated off being higher than that in all other distillation columns of (B1). In a manner similar to that described in WO 91/01981, it is advantageous firstly to separate off a fraction enriched with tetrahydrofuran and also with water and/or with esterification alcohol (if maleic esters have been used) at a low pressure. This is subsequently redistilled at a higher pressure, enabling tetrahydrofuran of high purity to be obtained (pure tetrahydrofuran product). The low-boiling fraction from the distillation column operated at higher pressure, which comprises the tetrahydrofuran which has not been separated off and also the water and/or the esterification alcohol, is advantageously recirculated to the first distillation column.

In the process of the present invention, preference is given to the following three assemblies of distillation columns.

(a) Dividing wall column (or thermally coupled conventional distillation columns)/dividing wall column (or thermally coupled conventional distillation columns)

In the first preferred arrangement, the distillation block (B1) comprises two dividing wall columns and/or a corresponding assembly of thermally coupled conventional distillation columns, where (i) fractionation into at least three fractions occurs in the first dividing wall column or the corresponding assembly of thermally coupled conventional distillation columns (K1a), (ii) the resulting tetrahydrofuran-enriched intermediate-boiling fraction is fractionated in the 45 second dividing wall column or the corresponding assembly of thermally coupled conventional distillation columns (K1b) to give at least three fractions, with tetrahydrofuran being isolated as intermediate-boiling fraction and the low-boiling fraction being recirculated to (K1a).

Figure 4:
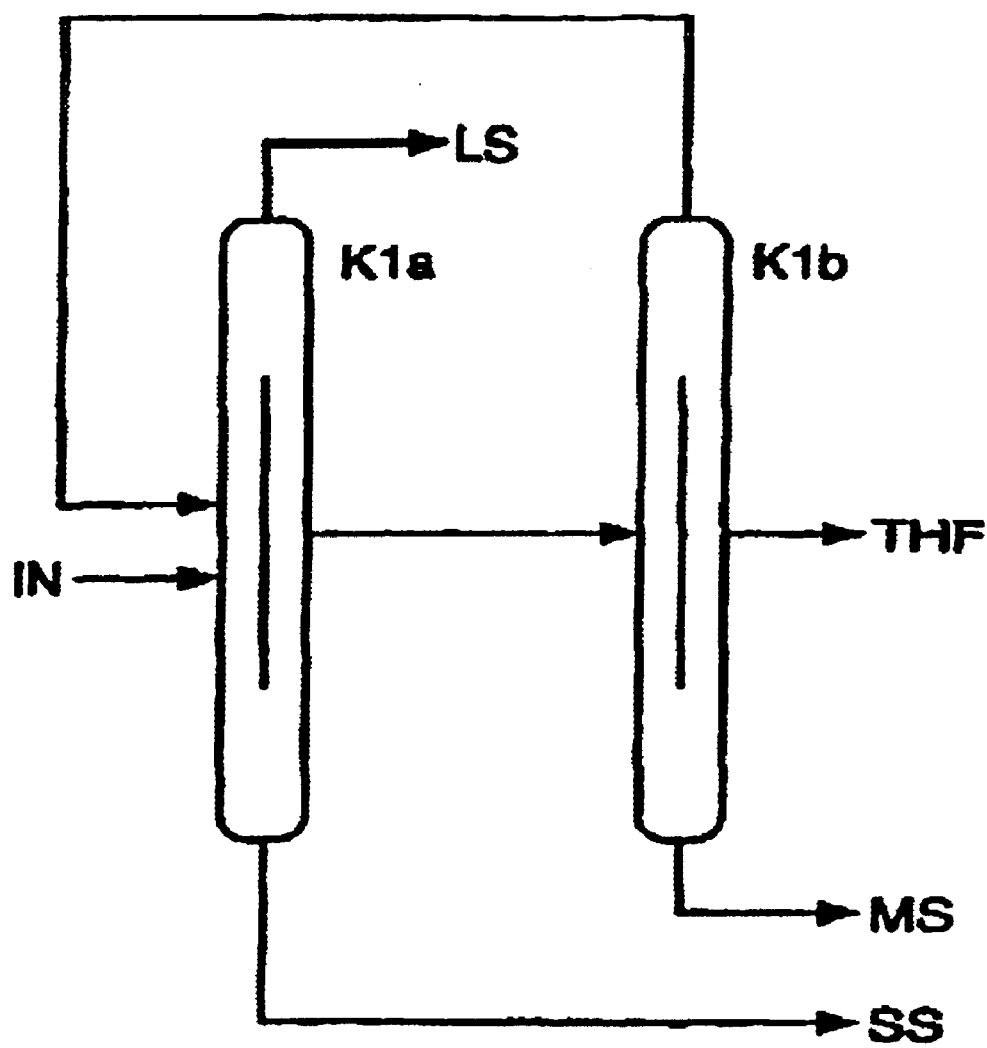
FIG. 4: is a schematic drawing of the first preferred arrangement.

A schematic drawing of the preferred arrangement is shown in FIG. 4. It should be pointed out that the presence of further apparatuses, for example pumps, heat exchangers or vessels, is also possible. The streams fed to or discharged from the assembly are denoted as follows:

(IN) Feed to the distillation block (B1). In a preferred embodiment, the feed corresponds to the mixture obtained in the hydrogenation of maleic anhydride, maleic acid, its diesters or its monoesters.

(THF) Tetrahydrofuran of high purity.

(LS) Low boilers, comprising by-products.

(MS) Intermediate boilers, comprising by-products.

(SS) High boilers, comprising by-products and generally γ-butyrolactone and 1,4-butanediol. To isolate the further desired products, this fraction is generally passed to the distillation block (B2) or (B3).

In (K1a), a tetrahydrofuran-enriched intermediate-boiling fraction is obtained from the feed (IN). This intermediate-boiling fraction comprises predominantly tetrahydrofuran and also water and/or the alcohol used as ester component in the hydrogenation. It is subsequently rectified at higher pressure in (K1b) to isolate the tetrahydrofuran of high purity (THF). At the top of (K1b), a mixture comprising tetrahydrofuran which has not been separated off and also water and/or the above-mentioned alcohol is taken off and recirculated to (K1a). This recycle stream can be fed into (K1a) together with the feed (IN). However, in terms of energy consumption, it is more advantageous to provide a separate introduction point which is preferably located above the feed inlet (IN). The fractions (LS) and (MS) are generally discharged from the distillation block. It may be advantageous to recirculate part of (MS) to (K1a). The high-boiling fraction (SS) is generally passed to the next distillation block for further work-up.

(b) Conventional distillation column/dividing wall column (or thermally coupled conventional distillation columns)

In the second preferred arrangement, the distillation block (B1) comprises an upstream conventional distillation column and a dividing wall column or a corresponding assembly of thermally coupled conventional distillation columns, where (i) fractionation into at least two fractions occurs in the first, conventional distillation column, (ii) the resulting tetrahydrofuran-enriched top fraction is fractionated in the dividing wall column or the corresponding assembly of thermally coupled conventional distillation columns (K1b) to give at least three fractions, with tetrahydrofuran being isolated as intermediate-boiling fraction and the low-boiling fraction being recirculated to the conventional distillation column.

Figure 5:
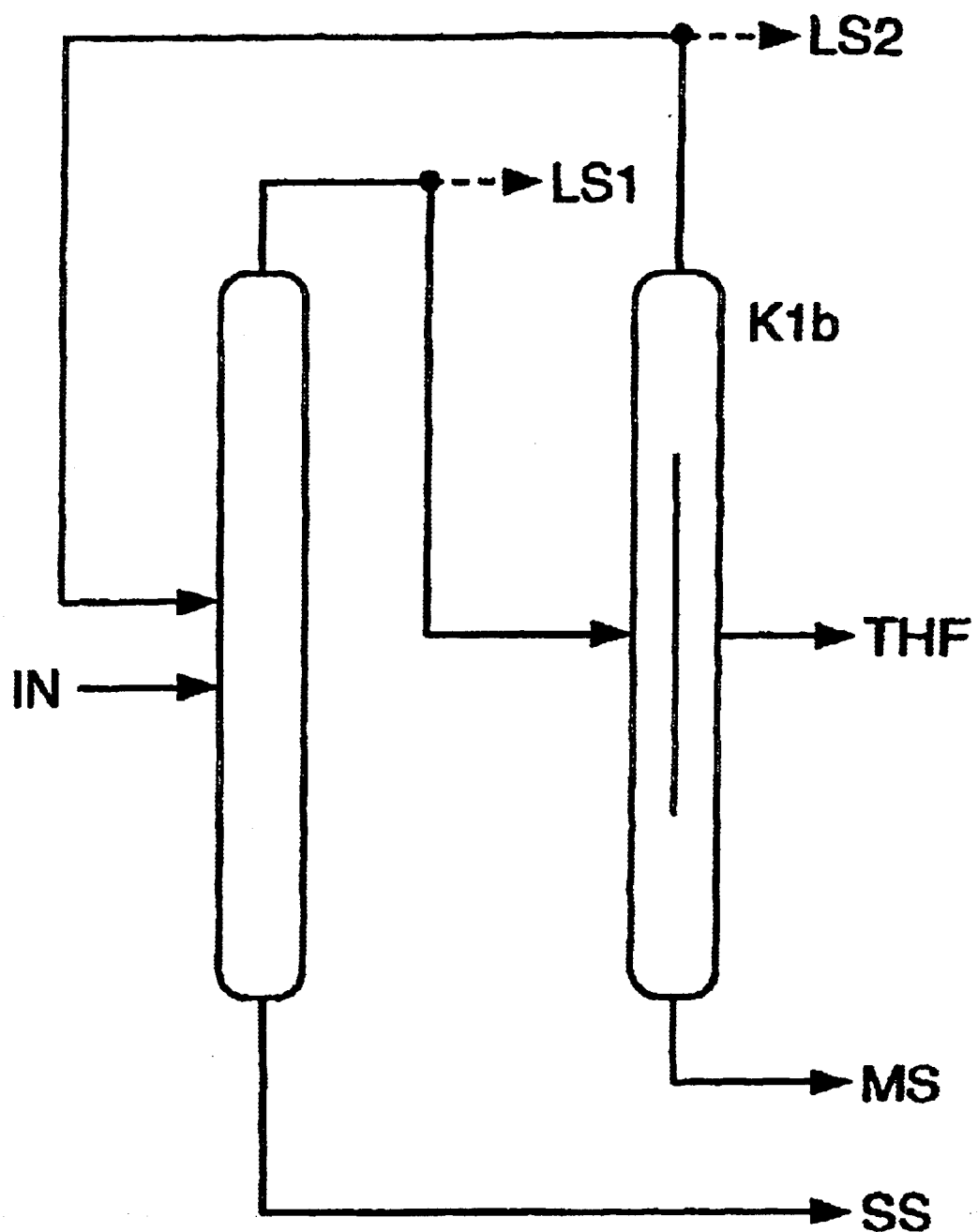
FIG. 5: is a schematic drawing of the second preferred arrangement.

A schematic drawing of the preferred arrangement is shown in FIG. 5. It should be pointed out that the presence of further apparatuses, for example pumps, heat exchangers or vessels, is also possible. The streams fed to or discharged from the assembly are denoted as follows:

(IN) Feed to the distillation block (B1). In a preferred embodiment, the feed corresponds to the mixture obtained in the hydrogenation of maleic anhydride, maleic acid, its diesters or its monoesters.

(THF) Tetrahydrofuran of high purity.

(LS1) Low boilers, comprising by-products.

(LS2) Low boilers, comprising by-products.

(MS) Intermediate boilers, comprising by-products.

(SS) High boilers, comprising by-products and generally γ-butyrolactone and 1,4-butanediol. To isolate the further desired products, this fraction is generally passed to the distillation block (B2) or (B3).

In this arrangement, two places for taking off the low boilers are possible. Depending on the embodiment, it is possible to remove the low boilers via (LS1), via (LS2) or in parallel via both points. The low boilers are preferably removed via (LS1) or (LS2).

In the first distillation column, a tetrahydrofuran-enriched low-boiling fraction is obtained from the feed (IN). It comprises predominantly tetrahydrofuran and also water and/or the alcohol used as ester component in the hydrogenation. It is subsequently rectified at higher pressure in (K1b) to isolate the tetrahydrofuran of high purity (THF). A mixture comprising tetrahydrofuran which has not been separated off and also water and/or the abovementioned alcohol is taken off at the top of (K1b) and is fed back into the first distillation column. This recycled stream can be introduced into the first distillation column together with the feed (IN). However, it is more advantageous in terms of energy consumption to provide a separate introduction point which is preferably above the feed inlet (IN). The fractions (LS1), (LS2) and (MS) are generally discharged from the distillation block. It may be advantageous to recirculate part of (MS) to the first distillation column. The high-boiling fraction (SS) is generally passed to the next distillation block for further work-up.

(c) Dividing wall column (or thermally coupled conventional distillation columns)/two conventional distillation columns connected in series In the third preferred arrangement, the distillation block (B1) comprises an upstream dividing wall column or a corresponding arrangement of thermally coupled conventional distillation columns followed by two conventional distillation columns connected in series, where (i) in the upstream dividing wall column or the corresponding assembly of thermally coupled conventional distillation columns (K1a), fractionation into at least three fractions occurs, (ii) the resulting tetrahydrofuran-enriched intermediate-boiling fraction is fractionated in the subsequent conventional distillation column to give at least two fractions, with the low-boiling fraction being recirculated to (K1a) and the tetrahydrofuran-enriched high-boiling fraction being (iii) fractionated in the second conventional distillation column to give at least two fractions, with tetrahydrofuran being isolated as low-boiling fraction.

Figure 6:
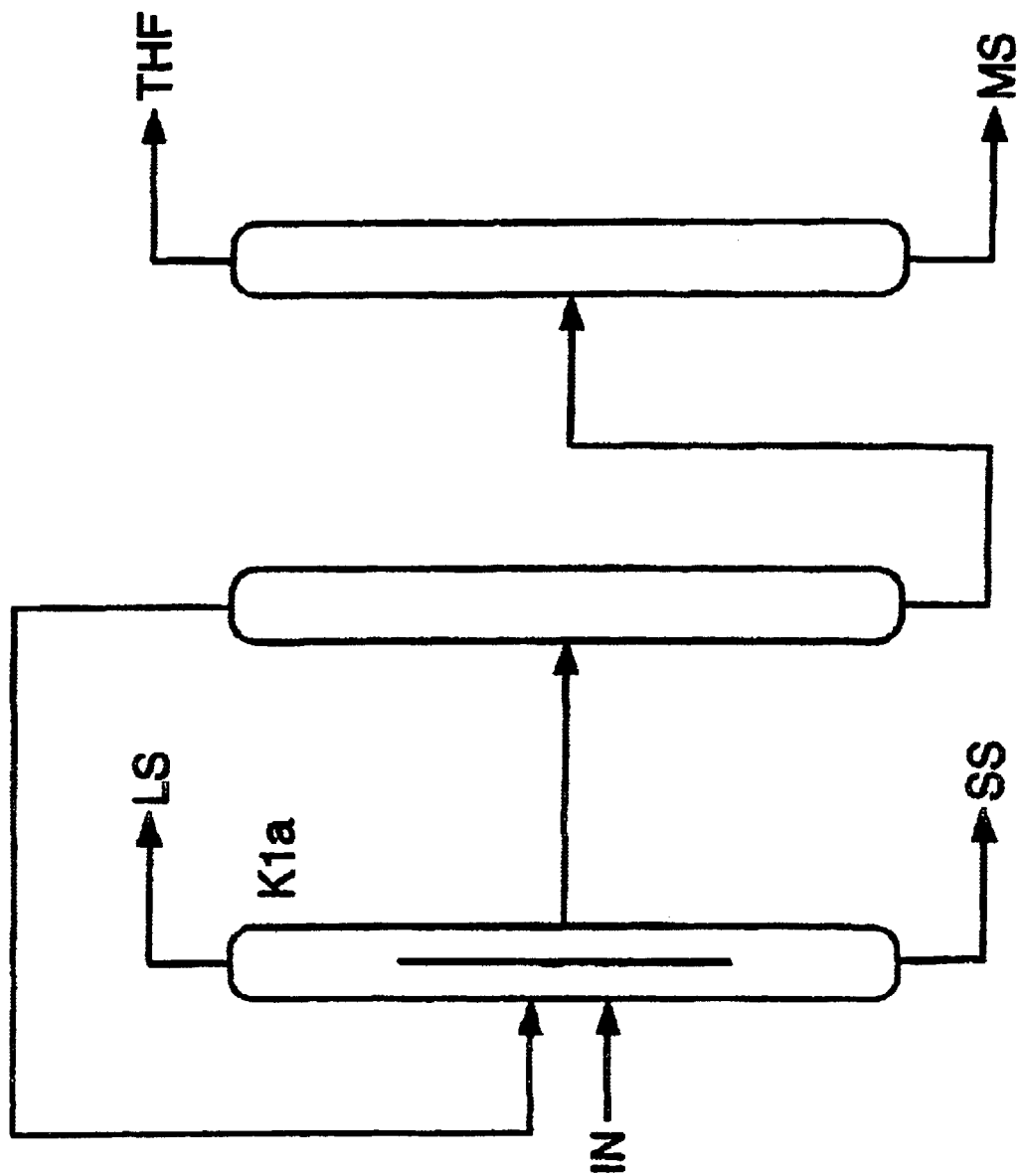
FIG. 6: is a schematic drawing of the third preferred arrangement.

A schematic drawing of the preferred arrangement is shown in FIG. 6. It should be pointed out that the presence of further apparatuses, for example pumps, heat exchangers or vessels, is also possible. The streams fed to or discharged from the assembly are denoted as follows:

(IN) Feed to the distillation block (B1). In a preferred embodiment, the feed corresponds to the mixture obtained in the hydrogenation of maleic anhydride, maleic acid, its diesters or its monoesters.

(THF) Tetrahydrofuran of high purity.

(LS) Low boilers, comprising by-products.

(MS) Intermediate boilers, comprising by-products.

(SS) High boilers, comprising by-products and generally γ-butyrolactone and 1,4-butanediol. To isolate the further desired products, this fraction is generally passed to the distillation block (B2) or (B3).

In (K1a), a tetrahydrofuran-enriched intermediate-boiling fraction is obtained from the feed (IN). It comprises predominantly tetrahydrofuran and also water and/or the alcohol used as ester component in the hydrogenation. It is fed to the subsequent conventional distillation column which is advantageously operated at a higher pressure. A mixture comprising tetrahydrofuran which has not been separated off and also water and/or the above-mentioned alcohol is taken off at the top and fed back to (K1a). This recycled stream can be introduced into the first distillation column together with the feed (IN). However, it is more advantageous in terms of energy consumption to provide a separate introduction point which is preferably above the feed inlet (IN). The high-boiling fraction from the first conventional distillation column is passed to the second conventional distillation column where the tetrahydrofuran of high purity (THF) is isolated via the top. The fractions (LS) and (MS) are generally discharged from the distillation block. It may be advantageous to recirculate part of (MS) to the first distillation column. The high-boiling fraction (SS) is generally fed to the subsequent distillation block for further work-up.

In the process of the present invention, particular preference is given to the two arrangements (a) dividing wall column (or thermally coupled conventional distillation columns)/dividing wall column (or thermally coupled conventional distillation columns) and (b) conventional distillation column/dividing wall column (or thermally coupled conventional distillation columns).

If a dividing wall column or a corresponding assembly of thermally coupled conventional distillation columns is used as first distillation column (K1a), as described under (a) or (c), this is preferably operated at an absolute pressure of from 0.05 to 0.2 MPa, particularly preferably at atmospheric pressure.

The individual subregions in (K1a) generally have the following number of theoretical plates:

Top section (1): preferably from 0 to 60, particularly preferably from 10 to 60;
upper feed section (2): preferably from 0 to 60, particularly preferably from 10 to 60;
upper offtake section (3): preferably from 0 to 60, particularly preferably from 10 to 60;
lower feed section (4): preferably from 0 to 30, particularly preferably from 1 to 25;
lower offtake section (5): preferably from 0 to 60, particularly preferably from 10 to 50;
bottom section (6): preferably from 0 to 60, particularly preferably from 1 to 40.

The total number of theoretical plates in the upper and lower feed section (2) and (4) in (K1a) is preferably from 80 to 110%, particularly preferably from 90 to 100%, of the total number of theoretical plates in the upper and lower offtake section (3) and (5).

(K1b), which is configured as a dividing wall column or as a corresponding assembly of thermally coupled conventional distillation columns and whose use is described by way of example in (a) and (b), is preferably operated at an absolute pressure of from 0.3 to 1.2 MPa, particularly preferably from 0.5 to 0.7 MPa.

The individual subregions in (K1b) generally have the following number of theoretical plates:

Top section (1): preferably from 0 to 60, particularly preferably from 10 to 60;
upper feed section (2): preferably from 0 to 60, particularly preferably from 10 to 60;
upper offtake section (3): preferably from 0 to 60, particularly preferably from 10 to 60;
lower feed section (4): preferably from 0 to 60, particularly preferably from 10 to 60;
lower offtake section (5): preferably from 0 to 60, particularly preferably from 10 to 60;
bottom section (6): preferably from 0 to 60, particularly preferably from 10 to 60.

The total number of theoretical plates in the upper and lower feed section (2) and (4) in (K1b) is preferably from 80 to 110%, particularly preferably from 90 to 100%, of the total number of theoretical plates in the upper and lower offtake section (3) and (5).

If a conventional distillation column is used as first distillation column, as described under (b), it is preferably operated at an absolute pressure of from 0.1 to 0.15 MPa, particularly preferably from 0.10 to 0.11 MPa. The subregion above the feed point generally has from 10 to 60 theoretical plates, preferably from 20 to 50 theoretical plates. The subregion below the feed point generally has from 5 to 30 theoretical plates, preferably from 10 to 25 theoretical plates.

In the arrangement described under (c), which has an upstream dividing wall column or a corresponding assembly of thermally coupled conventional distillation columns followed by two conventional distillation columns connected in series, the first of the two conventional distillation columns is preferably operated at an absolute pressure of from 0.5 to 1.0 MPa, particularly preferably from 0.4 to 0.8 MPa. The subregion above the feed point generally has from 0 to 30 theoretical plates, preferably from 0 to 20 theoretical plates. The subregion below the feed point generally has from 20 to 50 theoretical plates, preferably from 20 to 40 theoretical plates. The second of the two conventional distillation columns is preferably operated at a pressure lower than that in the first column. Preference is given to an absolute pressure of from 0.1 to 0.15 MPa, particularly preferably from 0.10 to 0.11 MPa and particularly preferably atmospheric pressure. The subregion above the feed point generally has from 10 to 30 theoretical plates, preferably from 15 to 25 theoretical plates. The subregion below the feed point generally has from 20 to 40 theoretical plates, preferably from 25 to 35 theoretical plates.

(B2) Distillation Block for Separating Off γ-butyrolactone

The γ-butyrolactone-containing mixture which is fed to the distillation block (B2) comes, for example, from the distillation block (B1). However, it is also possible for the mixture to originate from other work-up units, e.g. distillation block (B3), or directly from the process for producing the mixture, e.g. the hydrogenation of maleic anhydride, maleic acid, its diesters or its monoesters.

In the process of the present invention, the distillation block for separating off γ-butyrolactone preferably comprises a dividing wall column or a corresponding assembly of thermally coupled conventional distillation columns (K2). In this distillation block, γ-butyrolactone is taken off at a side offtake (B), preferably in liquid form. At the top of the column, low-boiling by-products (A) are taken off. Depending on the composition of the feed mixture and the configuration of the fractional distillation, all or part of these low-boiling products is discharged or recirculated to the synthesis steps preceding the work-up by distillation.

(K2) is preferably operated at an absolute pressure of from 0.001 to 0.15 MPa, particularly preferably from 0.01 to 0.02 MPa.

The individual subregions in (K2) generally have the following number of theoretical plates:

Top section (1): preferably from 10 to 100, particularly preferably from 15 to 95;
upper feed section (2): preferably from 10 to 100, particularly preferably from 15 to 95;
upper offtake section (3): preferably from 10 to 100, particularly preferably from 15 to 95;
lower feed section (4): preferably from 10 to 100, particularly preferably from 15 to 95;
lower offtake section (5): preferably from 10 to 100, particularly preferably from 15 to 95;
bottom section (6): preferably from 10 to 100, particularly preferably from 15 to 95.

The total number of theoretical plates in the upper and lower feed section (2) and (4) in (K2) is preferably from 80 to 110%, particularly preferably from 90 to 100%, of the total number of theoretical plates in the upper and lower offtake section (3) and (5).

(B3) Distillation Block for Separating Off 1,4-butanediol

The 1,4-butanediol-containing mixture which is fed to the distillation block (B3) comes, for example, from the distillation block (B2). However, it is also possible for the mixture to originate from other work-up units, e.g. distillation block (B1), or directly from the process for producing the mixture, e.g. the hydrogenation of maleic anhydride, maleic acid, its diesters or its monoesters.

In the process of the present invention, the distillation block for separating off 1,4-butanediol preferably comprises a dividing wall column or a corresponding assembly of thermally coupled conventional distillation columns (K3). In this distillation block, 1,4-butanediol is taken off at a side offtake (B), preferably in liquid form. At the top of the column, low-boiling by-products (A) are taken off. Depending on the composition of the feed mixture and the configuration of the fractional distillation, all or part of these low-boiling products is discharged or recirculated to the preceding distillation blocks (B1) or (B2). However, it is also possible to concentrate the 9 bottom product (C) further in an optional, downstream distillation column or evaporator, preferably a falling film evaporator or a thin film evaporator, and to recover further amounts of 1,4-butanediol in this way.

(K3) is preferably operated at an absolute pressure of from 0.001 to 0.05 MPa, particularly preferably from 0.003 to 0.01 MPa.

The individual subregions in (K3) generally have the following number of theoretical plates:

Top section (1): preferably from 10 to 100, particularly preferably from 15 to 95;
upper feed section (2): preferably from 10 to 100, particularly preferably from 15 to 95;
upper offtake section (3): preferably from 10 to 100, particularly preferably from 15 to 95;
lower feed section (4): preferably from 10 to 100, particularly preferably from 15 to 95;
lower offtake section (5): preferably from 10 to 100, particularly preferably from 15 to 95;
bottom section (6): preferably from 10 to 100, particularly preferably from 15 to 95.

The total number of theoretical plates in the upper and lower feed section (2) and (4) in (K3) is preferably from 80 to 110%, particularly preferably from 90 to 100%, of the total number of theoretical plates in the upper and lower offtake section (3) and (5).

All the dividing wall columns and thermally coupled conventional distillation columns used in the process of the present invention can be provided with distillation packing or with distillation trays as column internals. Explicit mention may be made of ordered packing, random packing, valve trays, sieve trays or bubble cup trays.

If the products need to meet high purity requirements, it is advantageous to use distillation packing. Owing to the specific separation properties, the use of ordered packings made of mesh or metal sheets is particularly advantageous.

In the case of distillation columns having an internal diameter of more than 1.2 m, economic considerations (capital costs) make it advisable to use distillation trays, unless there are overriding reasons for not using them. In the case of conventional distillation columns, valve trays, sieve trays and bubble cup trays are suitable, while in the case of dividing wall columns suitable trays are valve trays and sieve trays.

In the process of the present invention, (K1a), (K1b), (K2) and (K3) are preferably equipped with ordered packing, random packing, valve trays, sieve trays and/or bubble cap trays whose pressure drop increases continually with increasing gas throughput by at least 20% per increase of the F factor by 0.5 $Pa^{0.5}$. The F factor is the product of the gas velocity and the root of the gas density (cf. Ullmann's Encyclopedia of Industrial Chemistry, 6th edition, 1999 Electronic Release, Chapter "Distillation and Rectification, Design and Dimensioning"). The preferred pressure drop behavior achieves an advantageous division of the rising gas stream from the bottom section (6) into the lower feed section (4) and the lower offtake section (5).

Owing to the excellent separation properties, (K2) and (K3) in the process of the present invention are particularly preferably equipped with ordered packing and/or random packing whose pressure drop increases continually with increasing gas throughput by at least 20% per increase of the F factor by 0.5 $Pa^{0.5}$. The preferred pressure drop behavior achieves an advantageous division of the rising gas stream from the bottom section (6) into the lower feed section (4) and the lower offtake section (5).

If the products need to meet particularly high purity requirements, it is advantageous to provide the dividing wall with thermal insulation. A description of various possible ways of doing this may be found, for example, in U.S. Pat. No. 5,785,819. A design having a narrow intermediate gas space is particularly advantageous. For this reason, the dividing wall in (K2) and (K3) in the process of the present invention is particularly preferably thermally insulated.

As described above and shown in FIGS. 1 to 3, the region within the dividing wall column or the corresponding assembly of thermally coupled conventional distillation columns can be roughly divided into the six subregions (1) to (6). Depending on the local separation task in the distillation column, different internals can be used within one column. Thus, a dividing wall column or a corresponding assembly of thermally coupled conventional distillation columns can contain different forms of distillation packing, different distillation trays or even both. Even within one of the six subregions, different distillation packings are possible.

The present invention further provides a control concept for regulating the process of the present invention.

Various control strategies have been described in the prior art for regulating dividing wall columns and corresponding assemblies of thermally coupled conventional distillation columns.

In the case of very simple separation tasks, for example in the case of two-component mixtures displaying ideal behavior in a conventional distillation column, mathematical modelling is possible in many cases. If further components are present or if the system does not behave ideally, a satisfactory simulation model is no longer obtained in many cases. The mathematical modelling of the fractionation of a multicomponent system in a dividing wall column or a corresponding assembly of thermally coupled conventional distillation columns is even more complex. Previously known modelling calculations tend to show the instability problems which may occur during operation rather than give practical information on the optimal regulation of a distillation column. For this reason, the models are frequently simplified on the basis of plausibility assessments and experimental results.

Thus, M. Knott, Process Engineering, Vol. 2, 1993, February, pages 33 to 34, describes a simplified simulation model in which the composition of the top product is regulated via the amount of side product taken off, the composition of the side product is regulated via the reflux ratio and the composition of the bottom product is regulated via the amount in which it is taken off. Carrying out the regulation nevertheless requires a complex, dynamic computer model. For the purposes of the present invention, it was recognized that in the case of the present objective, namely the fractional distillation of mixtures obtained in the hydrogenation of maleic anhydride, maleic acid, its diesters or its monoesters to give at least three fractions of which at least one fraction comprises tetrahydrofuran, γ-butyrolactone and/or 1,4-butanediol, the previously described control concept can achieve neither the necessary high purity of the desired products in the side offtake streams nor the required stability in the case of fluctuations in the amount of the product streams and their composition.

E. A. Wolff et al., Ind. Eng. Chem. Res. 34, 1995, pages 2094 to 2103, reports the modelling of the fractionation of three-component mixtures in dividing wall columns. Here, it is recognized that, especially in those cases in which a high product purity is sought, serious problems are to be expected. A solution suggested is a comprehensive mathematical analysis which has to be carried out for each individual case. It goes without saying that such a control concept for the fractionation of a multicomponent mixture cannot be used industrially.

U.S. Pat. No. 4,230,533 teaches control of a dividing wall column via the concentration of the low-boiling component in the lower feed section as control parameter for the division of the relative gas and liquid flows between the lower feed section and the lower offtake section. For the purposes of the present invention, it was recognized that this simplified control concept can achieve neither the high purity of the desired products in the side offtake streams required according to the present objectives nor the required stability in the case of fluctuations in the amount of the product streams and their composition.

DE-A 35 22 234 describes a method of operating a dividing wall column in an energy-efficient fashion. The key aspect of the disclosure is a targeted division of the liquid stream at the upper end of the dividing wall between upper feed section and upper offtake section. Only low boilers and intermediate boilers may leave the feed section in an upward direction and only high boilers and intermediate boilers may leave the feed section in a downward direction. Only under these conditions is it possible to operate the column in an energy-efficient fashion while at the same time meeting high purity requirements. The division of the liquid stream is regulated via the four temperatures of the upper and lower feed section and the upper and lower offtake section as measured parameters. For the purposes of the present invention, it was recognized that this control concept, too, can achieve neither the high purity of the desired products in the side offtake streams required according to the present objectives nor the required stability in the case of fluctuations in the amount of the product streams and their composition.

EP-A 0 780 147 discloses a concept for regulating a dividing wall column or a corresponding assembly of thermally coupled conventional distillation columns which makes recourse to the measurement of concentrations of the components to be separated in the region of the distillation column and formulates control actions from these values.

The control concept of the present invention for the dividing wall columns and/or the corresponding assembly of thermally coupled conventional distillation columns used in the process of the present invention can be used in the case of all dividing wall columns and/or corresponding assemblies of thermally coupled conventional distillation columns employed in the process of the present invention. The control concept of the present invention is preferably used for the columns (K1a), (K1b), (K2) and (K3).

(a) The ratio of the downflowing liquid stream at the upper end of the upper feed section (2) to the downflowing liquid stream at the upper end of the upper offtake section (3) is preferably from 0.1 to 1.0, particularly preferably from 0.3 to 0.6. This makes it possible to locate the dividing wall centrally, which leads to constructional advantages.

The targeted division of the liquid stream flowing downward at the top section (1) is preferably achieved by the liquid stream being collected in a collection space located inside or outside the distillation column and being divided by means of a fixed setting or a regulator. This also includes the function of passing on the liquid, for example by the function of a pump reservoir or by ensuring a sufficiently high head of liquid. The targeted division can be carried out, for example, by means of flow-regulated pumps and/or flow-regulated control devices, for example valves. The divided liquid streams are then conveyed into the two column regions (2) and (3). In the case of distillation columns having distillation trays as internals (referred to as tray columns) it is particularly useful to enlarge the downflow shaft to about two or three times the customary height and to store the corresponding amount of liquid in it. In the case of distillation columns having distillation packing as internals (referred to as packed columns), the liquid is firstly collected in collectors and from there conveyed to an internal or external collection space.

Figure 7:
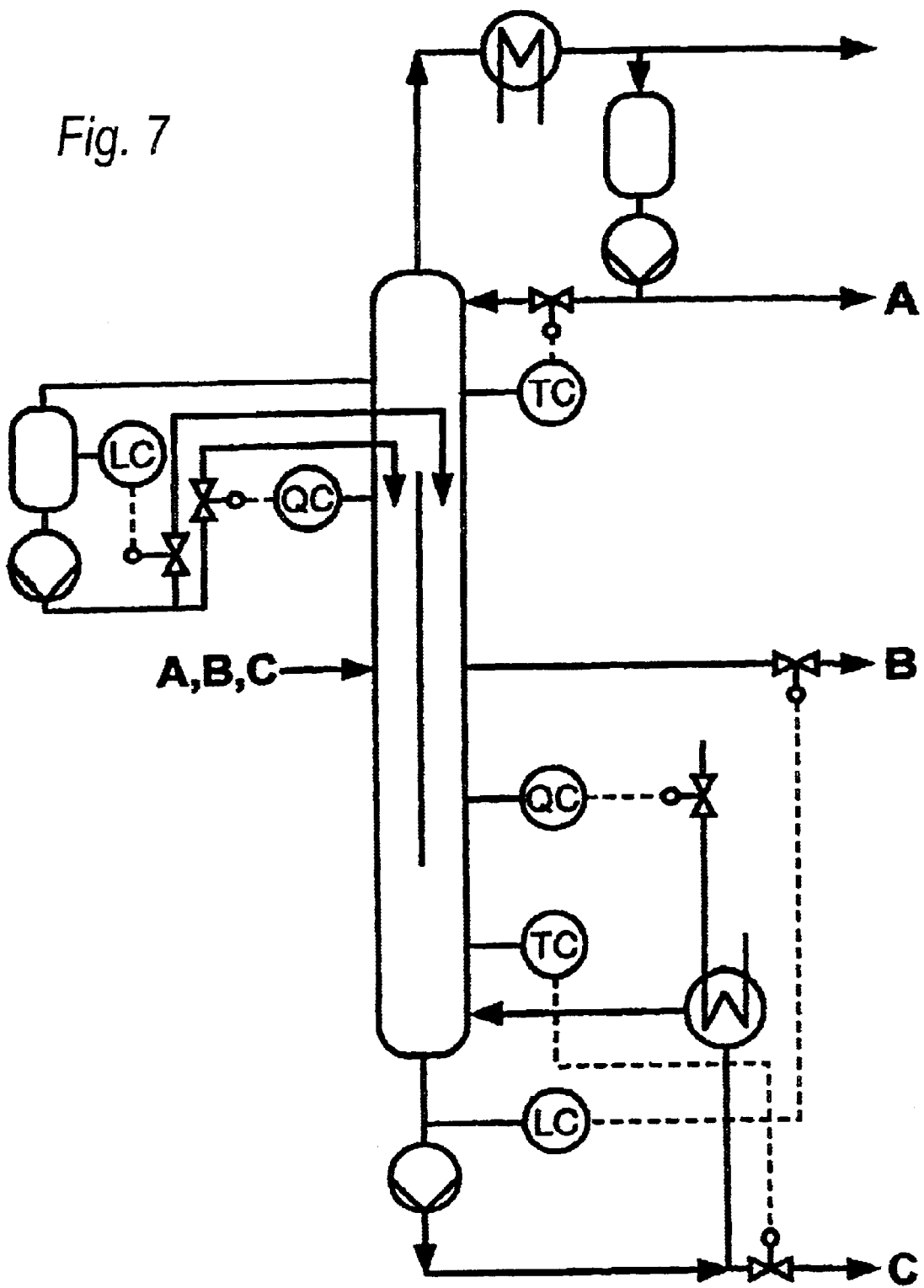
FIG. 7: shows a nonlimiting, schematic diagram illustrating integration and control.

A nonlimiting, schematic diagram illustrating integration and control is shown in FIG. 7.

(b) The ratio of the vapor stream at the lower end of the lower feed section (4) to the vapor stream at the lower end of the lower offtake section (5) is preferably from 0.8 to 1.2, particularly preferably from 0.85 to 1.15. This makes it possible for the dividing wall to be advantageously located centrally.

The targeted division of the vapor stream flowing upward at the bottom section (6) is preferably achieved by selection of suitable separation internals and/or the additional installation of internals which produce a pressure drop, for example iris diaphragms.

c) The liquid flow to the feed point is preferably set by means of a flow regulator so that the total liquid stream flowing into the feed section (2) and (4) cannot drop below 30% of the design value. Here, the design value is the value for which the column has been designed or calculated thermodynamically and fluid-dynamically.

This measure keeps the distillation column in a stable operating region and ensures the high purity of the desired products.

The flow regulation measure according to the present invention is preferably achieved by conveying the liquid stream to the feed point from an intermediate reservoir by means of a pump or a static head of at least 1 m. This avoids, in particular, short-term fluctuations in the amount introduced, which could otherwise lead to sometimes sensitive fluctuations in the operating state of the distillation column and thus could endanger the continuously high purity of the desired products.

(d) The downflowing liquid stream at the lower end of the upper offtake section (3) is preferably divided between the liquid stream discharged at the offtake and the liquid stream flowing into the lower offtake section (5) by means of a regulator so that the liquid stream flowing into the lower offtake section (5) cannot drop below 30% of the design value. Here, the design value is the value for which the column has been designed or calculated thermodynamically and fluid-dynamically.

In the fractionation of multicomponent mixtures into a low-boiling fraction, an intermediate-boiling fraction and a high-boiling fraction, there are usually specifications concerning the maximum permissible amount of low boilers and high boilers in the intermediate-boiling fraction. Here, individual values are specified for components critical to the separation problem, referred to as key components, or the total of a plurality of key components is specified. In points (e) and (f), the control concept of the present invention in respect of the setting of the undesirable high-boiling and low-boiling components in the side product (intermediate-boiling fraction) is described.

(e) The split ratio of the downflowing liquid stream at the upper end of the upper feed section (2) to the downflowing liquid stream at the upper end of the upper offtake section (3) is preferably set so that the concentration of a high-boiling component for which a particular limit value is to be achieved in the liquid stream from the side offtake point (side product) is from 10 to 80%, preferably from 30 to 50%, of this limit value the liquid and/or gas phase, preferably in the liquid phase, at the lower end of the top section (1), and the split ratio is increased in favor of the upper feed section (2) when the concentration of the high-boiling component for which a particular limit value is to be achieved in the liquid stream from the side offtake (side product) at the lower end of the top section (1) is increased, and the split ratio is decreased in respect of the upper feed section (2) when the concentration of the high-boiling component for which a particular limit value is to be achieved in the liquid stream from the side offtake (side product) at the lower end of the top section (1) is decreased.

This measure ensures the high purity of the desired product in the side product in respect of the undesirable high-boiling component even in the case of fluctuations in the quality and composition of the feed to the column or in the case of unstable operation of the distillation column.

If more than one undesirable high-boiling component are present, it is the high-boiling component which is most likely to endanger adherence to the limit value in the side product which is decisive for the control procedure. If the concentration of this high-boiling component at the lower end of the top section (1) rises above the respective maximum permissible concentration, the split ratio is to be increased in favor of the upper feed section (2). If the concentration of this high-boiling component at the lower end of the top section (1) decreases, the split ratio can generally be decreased in respect of the upper feed section (2). However, this is all only to such an extent that these and all further undesirable high-boiling components do not exceed the respective maximum permissible concentration at the lower end of the top section (1) and thus ensure adherence to the limit values in the side product. The determination of the concentrations of the high-boiling components (analysis) can be carried out continuously or at intervals. It can be carried out either inside or outside the distillation column. If it is carried out outside the distillation column, a gaseous and/or liquid sample has to be taken continuously or at intervals. If the samples have not been consumed or changed by the analysis, or more samples than necessary have been taken, it is likewise possible to return the sample to the distillation column. Examples of suitable analytical methods are chromatographic methods (e.g. gas chromatography) or optical methods (e.g. infrared spectroscopy). The analytical methods can advantageously be integrated into the automatic control circuit, so that the measurement result is used as control parameter for division of the liquid.

When using the preferred mixture, which originates from the hydrogenation of maleic anhydride, maleic acid, its diesters or its monoesters, typical high-boiling components which have to be regulated under the control concept described are, for example, 1,4-butanediol in (K2) and dibutylene glycol (bis(4-hydroxybutyl) ether) in (K3).

A nonlimiting, schematic diagram illustrating integration and control is shown in FIG. 7.

(f) The heating power of the vaporizer on the bottom section (6) is preferably set so that the concentration of a low-boiling component for which a particular limit value is to be achieved in the liquid stream of the side offtake point (side product) is from 10 to 80%, preferably from 30 to 50%, of this limit value in the liquid and/or gas phase at the upper end of the bottom section (6), and the heating power of the vaporizer on the bottom section (6) is increased when the concentration of the low-boiling component for which a particular limit value is to be achieved in the liquid stream from the side offtake (side product) at the upper end of the bottom section (6) is increased, and the heating power of the vaporizer on the bottom section (6) is reduced when the concentration of the low-boiling component for which a particular limit value is to be achieved in the liquid stream from the side offtake (side product) at the upper end of the bottom section (6) is decreased.

This measure ensures the high purity of the desired product in the side product in respect of the undesirable low-boiling component even in the case of fluctuations in the quality and composition of the feed to the column or in the case of unstable operation of the distillation column.

If more than one undesirable low-boiling component are present, it is the low-boiling component which is most likely to endanger adherence to the limit value in the side product which is decisive for the control procedure. If the concentration of this low-boiling component at the upper end of the bottom section (6) increases, the heating power of the vaporizer on the bottom section (6) is to be increased. If the concentration of this low-boiling component at the upper end of the bottom section (6) decreases, the heating power of the vaporizer on the bottom section (6) can generally be decreased. However, this is all only to such an extent that these and all further undesirable low-boiling components do not exceed the respective maximum permissible concentration at the upper end of the bottom section (6) and thus ensure adherence to the limit values in the side product.

As regards the determination of the concentrations of the low-boiling components, what has been said on this subject in point (e) applies in principle and may be regarded as incorporated at this point, too.

When using the preferred mixture originating from the hydrogenation of maleic anhydride, maleic acid or its diesters or its monoesters, typical low-boiling components for the purposes of the above-described regulation method are, for example, water in (K2) and γ-butyrolactone in (K3).

A nonlimiting, schematic diagram illustrating integration and control is shown in FIG. 7.

(g) The top product is preferably taken off in a temperature-regulated fashion, using a temperature measurement point in the top section (1) for regulation. The temperature measurement point used is preferably located from 3 to 8, particularly preferably from 4 to 6, theoretical plates below the upper end of the top section (1).

The direct control parameter for the regulated offtake of the top product can be the amount of top product discharged, the reflux ratio or preferably the amount of runback.

A nonlimiting, schematic diagram illustrating integration and control is shown in FIG. 7.

h) The bottom product is preferably taken off in a temperature-regulated fashion, using a temperature measurement point in the bottom section (6) for regulation. The temperature measurement point used is preferably located from 3 to 8, particularly preferably from 4 to 6, theoretical plates above the lower end of the bottom section (6).

The direct control parameter for the regulated offtake of the bottom product can be the amount of bottom product discharged.

A nonlimiting, schematic diagram illustrating integration and control is shown in FIG. 7.

(i) The liquid stream taken off at the side offtake point (side product) is preferably taken off in a level-regulated fashion, using the liquid level in the vaporizer on the bottom section (6) as control parameter.

A nonlimiting, schematic diagram illustrating integration and control is shown in FIG. 7.

As mentioned at the outset, the control concept of the present invention has at least one, preferably more than one, of the features (a) to (i). The combination of all features (a) to (i) is particularly preferred.

FIG. 7 schematically shows the integration of the various apparatuses and measurement points into a dividing wall column and its instrumentation. The designation of the instrumentation items is according to the usual convention. Meanings of the letters are:

L liquid level

Q analytical value (concentration of a component i or alternatively an integrated measured parameter, e.g. index of refraction or temperature)

T temperature.

"C" denotes a control function, i.e. a control signal is produced by a corresponding regulator (broken line).

Compared to the control concepts of the prior art, the control concept of the present invention makes it possible to achieve a high purity of the desired products at the side offtakes and a flexible and at the same time simple operating procedure which ensures reliable operation of the process with adherence to the high purity requirements and a low energy consumption even in the case of fluctuations in the amount of the product streams and their composition.

In the process of the present invention, the fractional distillation is particularly preferably carried out in three distillation blocks which comprise four dividing wall columns or corresponding assemblies of thermally coupled conventional distillation columns (K1a), (K1b), (K2) and (K3), where in distillation block (B1) tetrahydrofuran is separated off by carrying out a fractionation into at least three fractions in (K1a), passing the tetrahydrofuran-enriched intermediate-boiling fraction to (K1b) and there carrying out a fractionation into at least three fractions, with tetrahydrofuran of high purity being able to be obtained as intermediate-boiling fraction and the low-boiling fraction being recirculated to (K1a), and passing the high-boiling fraction from (K1a) to the distillation block (B2), where in distillation block (B2) γ-butyrolactone is separated off by carrying out a fractionation into at least three fractions in (K2), with γ-butyrolactone of high purity being able to be isolated as intermediate-boiling fraction and the high-boiling fraction being passed to the distillation block (B3), where in distillation block (B3) 1,4-butanediol is separated off by carrying out a fractionation into at least three fractions in (K3), with 1,4-butanediol of high purity being able to be obtained as intermediate-boiling fraction.

Figure 8:
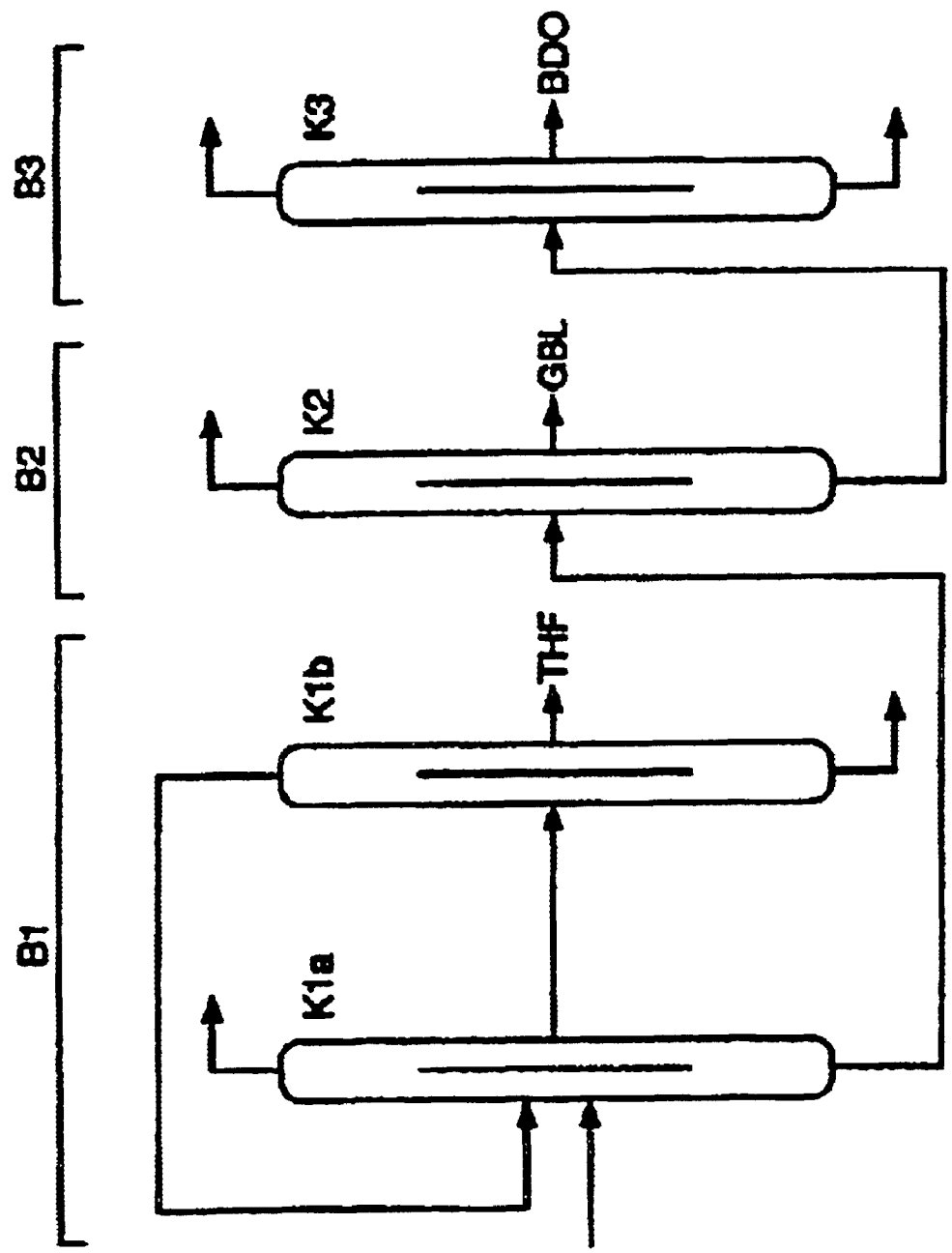
FIG. 8: is a schematic drawing of the fourth preferred arrangement.

This arrangement is shown schematically in FIG. 8. The three desired products are abbreviated as follows (THF) Tetrahydrofuran of high purity.

(GBL) γ-Butyrolactone of high purity.

(BDO) 1,4-Butanediol of high purity.

It may be explicitly pointed out that the assembly may include further apparatuses, for example further distillation columns, pumps, heat exchangers or vessels, in addition to the four dividing wall columns or the corresponding assemblies of thermally coupled conventional distillation columns.

Furthermore, particular preference is also given in the process of the present invention to assemblies which are derived from the above-described assembly of three distillation blocks (B1–B2–B3) by omission of one or two distillation blocks. Specifically, this means the combinations (B1), (B2), (B3), (B1–B2), (B1–B3) and (B2–B3). In these cases, not all three of the products tetrahydrofuran, γ-butyrolactone and 1,4-butanediol are isolated, but only two or even one of them.

In a preferred embodiment, use is made of an arrangement comprising the three distillation blocks (B1) distillation block for separating off tetrahydrofuran, which makes it possible to carry out a fractionation into at least three fractions in the dividing wall column or the corresponding assembly of thermally coupled conventional distillation columns (K1a), where the tetrahydrofuran-enriched intermediate-boiling fraction is passed to the dividing wall column or the corresponding assembly of thermally coupled conventional distillation columns (K1b) in which it can be fractionated into at least three fractions, with tetrahydrofuran of high purity being able to be isolated as intermediate-boiling fraction and the low-boiling fraction being able to be recirculated to (K1a);

(B2) distillation block for separating off γ-butyrolactone, which makes it possible to carry out a fractionation into at least three fractions in the dividing wall column or the corresponding arrangement of thermally coupled conventional distillation columns (K2), with γ-butyrolactone of high purity being able to be isolated as intermediate-boiling fraction;

(B3) distillation block for separating off 1,4-butanediol, which makes it possible to carry out a fractionation into at least three fractions in the dividing wall column or the corresponding assembly of thermally coupled conventional distillation columns (K3), with 1,4-butanediol of high purity being able to be isolated as intermediate-boiling fraction;

in the order (B1) before (B2) before (B3). This arrangement is schematically shown in FIG. 8. The columns are configured as described above and are preferably provided with ordered packing. The columns are preferably operated within the range of the abovementioned operating parameters.

A mixture originating from the hydrogenation of maleic anhydride, maleic acid, its diesters or its monoesters and comprising the desired products tetrahydrofuran, γ-butyrolactone and 1,4-butanediol together with water and various by-products is fed in continuously at the side feed point of (K1a). At the top, the low boilers, for example butadiene, 2,3-dihydrofuran or methacrolein, are taken off and discharged from the plant. The intermediate-boiling fraction, which is enriched in tetrahydrofuran, is passed to (K1b). Tetrahydrofuran of high purity is isolated as intermediate-boiling fraction. The low-boiling fraction from (K1b), which comprises water and tetrahydrofuran which has not been separated off, is recirculated to (K1a). The high-boiling fraction of (K1b) is discharged from the plant. The high-boiling fraction from (K1a), which comprises the desired products γ-butyrolactone and 1,4-butanediol, is fed to (K2).

At the top of (K2), the low boilers, for example water or methanol, are taken off and discharged from the plant. γ-Butyrolactone of high purity is isolated as intermediate-boiling fraction. The high-boiling fraction from (K2), which comprises the desired product 1,4-butanediol, is fed to (K3).

At the top of (K3), the low boilers, for example acetals (e.g. 4-tetrahydrofuran-2-yloxybutanol), are taken off and discharged from the plant. 1,4-Butanediol of high purity is isolated as intermediate-boiling fraction. The high-boiling fraction from (K3), which comprises, for example, dibutylene glycol, is discharged from the plant.

The columns are preferably regulated according to the above-described control concept.

The process of the present invention makes it possible to prepare tetrahydrofuran, γ-butyrolactone and/or 1,4-butanediol continuously in high purity by fractional distillation of mixtures obtained in the hydrogenation of maleic anhydride, maleic acid, its diesters or its monoesters, with low energy consumption and low capital costs for the plant. Furthermore, the process of the present invention makes possible a flexible and at the same time simple operating procedure which ensures reliable operation of the process with adherence to the high purity requirements and with a low energy consumption even in the case of fluctuations in the amount of the product streams and their composition.

We claim:

1. A process for the continuous fractional distillation of a mixture comprising tetrahydrofuran, γ-butyrolactone and/or 1,4-butanediol to give at least three fractions, said fractions comprising a low boiling fraction, an intermediate-boiling fraction and a high boiling fraction, wherein the fractional distillation is carried out in an assembly of distillation columns comprising at least one dividing wall column or at least one assembly of thermally coupled distillation columns, each dividing wall column and each assembly of thermally coupled columns comprising a top section (1),
an upper feed section (2),
an upper offtake section (3),
a lower feed section (4),
a lower offtake section (5), and
a bottom section (6), which sections, during fractional distillation, comprise a stream of downflowing liquid and a stream of vapor, and wherein said assembly of distillation columns comprises at least one distillation block selected from the group consisting of (B1) a distillation block for separating off tetrahydrofuran, (B2) a distillation block for separating off γ-butyrolactone, and (B3) a distillation block for separating off 1,4-butanediol, and the products being isolated in the order (B1) before (B2) before (B3), corresponding to their boiling points.

2. A process as claimed in claim 1, wherein the mixture is obtained by hydrogenating maleic anhydride, maleic acid, its diesters or its monoesters.

3. A process as claimed in claim 1, wherein the distillation block (B1) comprises at least two distillation columns and the column in which tetrahydrofuran is separated off is operated at a higher pressure than all other distillation columns of (B1).

4. A process as claimed in claim 3, wherein the distillation block (B1) comprises an upstream distillation column and a dividing wall column or a corresponding assembly of thermally coupled distillation columns, and tetrahydrofuran is separated off by (a) fractionating the mixture into at least two fractions in the upstream distillation column to obtain a tetrahydrofuran-enriched top fraction, and (b) fractionating the tetrahydrofuran-enriched top fraction in the dividing wall column or the corresponding assembly of thermally coupled distillation columns (K1b) to give at least three fractions comprising an intermediate-boiling fraction of tetrahydrofuran and a low-boiling fraction, and recirculating said low-boiling fraction to the upstream distillation column.

5. A process as claimed in claim 3, wherein the distillation block (B1) comprises two dividing wall columns and/or a corresponding assembly of thermally coupled distillation columns, and tetrahydrofuran is separated off by (a) fractionating the mixture into at least three fractions in a first dividing wall column or in a corresponding assembly of thermally coupled distillation columns (K1a) to obtain a tetrahydrofuran-enriched intermediate-boiling fraction, and (b) fractionating the tetrahydrofuran-enriched intermediate-boiling fraction in a second dividing wall column or in a corresponding assembly of thermally coupled distillation columns (K1b) to give at least three fractions comprising an intermediate-boiling fraction of tetrahydrofuran and a low-boiling fraction, and recirculating said low-boiling fraction to (K1a).

6. A process as claimed in claim 5, wherein the column (K1b) is operated at an absolute pressure of from 0.3 to 1.2

MPa, said column (K1b) having a number of theoretical plates in sections (2), (3), (4) and (5), and the total number of theoretical plates in sections (2) and (4) is from 80 to 110% of the total number of theoretical plates in sections (3) and (5).

7. A process as claimed in claim 5, wherein the column (K1a) is operated at an absolute pressure of from 0.05 to 0.2 MPa, said column (K1a) having a number of theoretical plates in sections (2), (3), (4) and (5), and the total number of theoretical plates in sections (2) and (4) is from 80 to 110% of the total number of theoretical plates in sections (3) and (5).

8. A process as claimed in claim 7, wherein at least one of the columns (K1a) and (K1b) is equipped with column internals which provide for a continuous pressure drop increase with increasing gas throughput, the pressure drop increasing by at least 20% per F factor increase by 0.5 $Pa^{0.5}$.

9. A process as claimed in claim 7, wherein the stream of downflowing liquid at an upper end of section (2) of the column (K1a), and the stream of downflowing liquid at an upper end of section (3) of (K1a) are in a ratio of from 0.1 to 1.0.

10. A process as claimed in claim 9, wherein the stream of downflowing liquid is collected at section (1) of the column (K1a) in a collection space located inside or outside of (K1a), and the collected liquid is divided into two parts by means of a fixed setting or a regulator, a first part of the collected liquid being introduced into section (2), and a second part of the collected liquid being introduced into section (3) of (K1a).

11. A process as claimed in claim 9, wherein the stream of vapor at a lower end of section (4) of the column (K1a) and the stream of vapor at a lower end of section (5) of (K1a) are in a ratio of from 0.8 to 1.2.

12. A process as claimed in claim 9, which comprises feeding the mixture to a feed point located between sections (2) and (4) of the column (K1a) and setting a feed flow by means of a flow regulator so that the stream of liquid entering sections (2) and (4) cannot drop below 30% of a value for which (K1a) is designed.

13. A process as claimed in claim 9, wherein the stream of downflowing liquid at a lower end of section (3) of the column (K1a) is divided into two parts by means of a regulator, one part being discharged at an offtake located between sections (3) and (5) of (K1a), and another part flowing into section (5) of (K1a) so that the stream of liquid flowing into section (5) cannot drop below 30% of a value for which (K1a) is designed.

14. A process as claimed in claim 1, wherein the distillation block (B2) comprises a dividing wall column or a corresponding assembly of thermally coupled distillation columns (K2), said column (K2) being operated at an absolute pressure of from 0.001 to 0.15 MPa, said column (K2) having a number of theoretical plates in sections (2), (3), (4) and (5), and the total number of theoretical plates in sections (2) and (4) is from 80 to 110% of the total number of theoretical plates in sections (3) and (5).

15. A process as claimed in claim 14, wherein the column (K2) is equipped with column internals which provide for a continuous pressure drop increase with increasing gas throughput, the pressure drop increasing by at least 20% per F factor increase by 0.5 $Pa^{0.5}$, and the column internals being ordered packings and/or random packing elements.

16. A process as claimed in claim 1, wherein the distillation block (B3) comprises a dividing wall column or a corresponding assembly of thermally coupled distillation columns (K3), said column (K3) being operated at an absolute pressure of from 0.001 to 0.05 MPa, said column (K3) having a number of theoretical plates in sections (2), (3), (4) and (5), and the total number of theoretical plates in sections (2) and (4) is from 80 to 110% of the total number of theoretical plates in sections (3) and (5).

17. A process as claimed in claim 1, wherein the fractional distillation is carried out in three distillation blocks which comprise four dividing wall columns or corresponding assemblies of thermally coupled distillation columns (K1a), (K1b), (K2) and (K3).

\* \* \* \* \*